United States Patent
Shetty

(10) Patent No.: US 9,511,495 B2
(45) Date of Patent: Dec. 6, 2016

(54) METHOD AND APPARATUS FOR REMOTE MONITORING

(71) Applicant: Samsung Electronics Co., Ltd, Gyeonggi-do (KR)

(72) Inventor: Krishna Shetty, Gyeonggi-do (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 219 days.

(21) Appl. No.: 13/786,046

(22) Filed: Mar. 5, 2013

(65) Prior Publication Data

US 2013/0245827 A1    Sep. 19, 2013

(30) Foreign Application Priority Data

Mar. 19, 2012 (KR) ........................ 10-2012-0027705

(51) Int. Cl.
| | |
|---|---|
| B25J 9/16 | (2006.01) |
| G06F 19/00 | (2011.01) |
| G05D 1/02 | (2006.01) |
| G08B 21/02 | (2006.01) |
| B25J 19/02 | (2006.01) |

(52) U.S. Cl.
CPC ............ *B25J 9/1697* (2013.01); *B25J 19/023* (2013.01); *G05D 1/0246* (2013.01); *G05D 1/0274* (2013.01); *G06F 19/3418* (2013.01); *G08B 21/02* (2013.01)

(58) Field of Classification Search
CPC ........ B25J 9/1697; B25J 19/023; G08B 21/02; G05D 1/0274; G05D 1/0246; G05D 1/12; G05D 2201/0207; A61G 12/00
See application file for complete search history.

(56) References Cited

U.S. PATENT DOCUMENTS

| | | | |
|---|---|---|---|
| 5,802,494 A * | 9/1998 | Kuno | ................................ 705/2 |
| 7,774,032 B2 | 8/2010 | Swan et al. | |
| 2003/0122676 A1 | 7/2003 | Cuijpers et al. | |
| 2005/0151844 A1 | 7/2005 | Chiao et al. | |
| 2005/0216126 A1 * | 9/2005 | Koselka et al. | .............. 700/259 |
| 2006/0064203 A1 * | 3/2006 | Goto et al. | .................... 700/245 |
| 2006/0103522 A1 | 5/2006 | Spencer | |
| 2006/0117362 A1 * | 6/2006 | Jones et al. | ................... 725/105 |
| 2007/0135962 A1 * | 6/2007 | Kawabe et al. | .............. 700/225 |
| 2009/0091617 A1 | 4/2009 | Anderson | |
| 2010/0017046 A1 * | 1/2010 | Cheung | .................. G01S 7/003 701/2 |

(Continued)

FOREIGN PATENT DOCUMENTS

KR    10-2003-0038960    5/2003

OTHER PUBLICATIONS

Cader et al, Interactive Autonomous Baby Sitting Robot, ICIA 2006, IEEE, pp. 423-429.*

(Continued)

*Primary Examiner* — Abby Lin

(57) ABSTRACT

A monitoring control method in an electronic device is provided. The method includes displaying an area map for monitoring, and determining a virtual boundary on the area map. The area map is a specific space of the indoor or outdoor and displays objects or articles that are within the specific space of the indoor or outdoor. The virtual boundary constitutes a movement area for a monitoring target therewithin.

19 Claims, 10 Drawing Sheets

(56) References Cited

U.S. PATENT DOCUMENTS

| | | |
|---|---|---|
| 2010/0060448 A1 | 3/2010 | Larsen et al. |
| 2010/0134612 A1 | 6/2010 | Pryor et al. |
| 2011/0306304 A1* | 12/2011 | Forutanpour et al. ..... 455/67.11 |
| 2012/0316680 A1* | 12/2012 | Olivier, III ........... G05D 1/0246 700/258 |
| 2013/0024025 A1* | 1/2013 | Hsu .............................. 700/259 |
| 2013/0035790 A1* | 2/2013 | Olivier, III ........... G05D 1/0246 700/246 |

OTHER PUBLICATIONS

Porikli et al, Heli-Tele: Road Extraction from Helicopter Video, Jun. 2005.*

* cited by examiner

METHOD AND APPARATUS FOR REMOTE MONITORING

CROSS-REFERENCE TO RELATED APPLICATION(S) AND CLAIM OF PRIORITY

The present application is related to and claims priority under 35 U.S.C. §119(a) to a Korean Patent Application No. 10-2012-0027705 filed on Mar. 19, 2012 in the Korean Intellectual Property Office, the contents of which are herein incorporated by reference.

TECHNICAL FIELD OF THE INVENTION

The present invention relates to a method and apparatus for remote monitoring individuals, primarily, who need to be taken care of, such as baby or child.

BACKGROUND OF THE INVENTION

Generally, babies cannot express their opinions through talking and in addition, they are difficult to move at their will. Therefore, when being hungry, when being tired, when a diaper is moistened, when being ached, when being sleepy and the like, the babies express their conditions through crying, and parents listen to babies' cries to check babies' conditions with naked eyes, thereby recognizing what the babies want and taking a necessary action. Accordingly, parents who bring a baby up should take care of a baby within the range of being capable of promptly checking a baby's condition.

On the other hand, there are many cases in which a child plays alone without recognizing a preset danger situation owing to the characteristic of children. Accordingly, when parents/guardian (hereinafter, "guardian") leaves beside a child to do housework activities and the like, the child may come near being in a preset danger situation while playing alone. However, the guardian is hard to continuously stay beside a baby and the child and, although possible once in a while, there is an inconvenience that the guardian has to take care of the care-receiver while doing his/her works. An Individual who needs to be taken care of is named as a care-receiver in this patent disclosure.

Meanwhile, the conventional art has proposed Korean Patent Laid-Open Publication No. 10-2003-0038960 disclosing a monitoring system based on the Internet for controlling a mobile robot and monitoring, Korean Patent No. 10-07214860000 entitled "Robot monitoring system for bypass communication and a monitoring method thereof" disclosing a technology for eliminating a monitoring shadow zone of a monitoring target area using a monitoring device and a monitoring robot that are installed in the monitoring target area and providing to a user through wireless communication, and the like. Korean Patent Laid-Open Publication No. 10-2003-0038960 and Korean Patent No. 10-07214860000 discloses a technology in which a monitoring device is simply located in a location that a user wants, monitors exterior intrusion and the like in the location, and transmits the intrusion together with a video to a corresponding terminal.

However, the conventional technologies are limited to simply take a photograph of a care-receiver in a corresponding location and transmits a photographed video to a terminal of a guardian.

SUMMARY OF THE INVENTION

To address the above-discussed deficiencies of the prior art, it is a primary object to provide an intelligent baby monitoring method and apparatus.

Another aspect of the present disclosure is to provide a method and apparatus for setting a virtual boundary on a district map and transmitting a monitoring event occurring within the set virtual boundary to a guardian, to monitor a care-receiver intelligently. The above aspects are achieved by providing a method and apparatus for baby monitoring.

According to one aspect of the present disclosure, a monitoring control method in an electronic device is provided. The method includes displaying an area map for monitoring, and determining a virtual boundary on the area map. The area map is a specific space of the indoor or outdoor, and displays objects or articles that are within the specific space of the indoor or outdoor. The virtual boundary constitutes a movement area for a monitoring target within the virtual boundary.

According to another aspect of the present disclosure, a monitoring method in a monitoring robot device is provided. The method includes receiving, from a user, an instruction of monitoring a monitoring target within a virtual boundary of an area map, along with information about the virtual boundary of the area map and information about the monitoring target, judging if the monitoring target is within the virtual boundary of the area map, and, when the monitoring target is within the virtual boundary of the area map, notifying the user of monitoring start and, when the monitoring target is out of the virtual boundary of the area map, notifying the user that the monitoring start has failed. The area map is a specific space of the indoor or outdoor, and displays objects or articles that are within the specific space of the indoor or outdoor. The virtual boundary designates a movement area for the monitoring target within the virtual boundary.

According to a further aspect of the present disclosure, an electronic device is provided. The electronic device includes a touch sensing display for sensing a touch, a memory for storing data and instructions, one or more processors for executing computer programs, and one or more modules stored in the memory and configured to be executable by the one or more processors. The module comprises an instruction of displaying an area map for monitoring on the touch sensing display, and determining a virtual boundary on the area map.

According to yet another aspect of the present disclosure, a monitoring robot device is provided. The device includes a controller and a communication unit. The controller receives, from a user, an instruction of monitoring a monitoring target within a virtual boundary of an area map, along with information about the virtual boundary of the area map and information about the monitoring target, and determines if the monitoring target is within the virtual boundary of the area map. When the monitoring target is within the virtual boundary of the area map, the communication unit notifies the user of monitoring start. When the monitoring target is out of the virtual boundary of the area map, the communication unit notifies the user that the monitoring start has failed. The area map is a specific space of the indoor or outdoor, and displays objects or articles that are within the specific space of the indoor or outdoor. The virtual boundary designates a movement area for the monitoring target within the virtual boundary.

Before undertaking the DETAILED DESCRIPTION OF THE INVENTION below, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, such a device may be implemented in hardware, firmware or software, or some combination of at least two of the same. It should be noted that the functionality associated with any particular controller may be centralized or distributed, whether locally or remotely. Definitions for certain words and phrases are provided throughout this patent document, those of ordinary skill in the art should understand that in many, if not most instances, such definitions apply to prior, as well as future uses of such defined words and phrases.

BRIEF DESCRIPTION OF THE DRAWINGS

For a more complete understanding of the present disclosure and its advantages, reference is now made to the following description taken in conjunction with the accompanying drawings, in which like reference numerals represent like parts.

DETAILED DESCRIPTION OF THE INVENTION

FIGS. 1 through 6, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged communication electronic device. Preferred embodiments of the present disclosure will be described herein below with reference to the accompanying drawings. In the following description, well-known functions or constructions are not described in detail since they would obscure the invention in unnecessary detail. And, terms described below, which are defined considering functions in the present disclosure, can be different depending on user and operator's intention or practice. Therefore, the terms should be defined on the basis of the disclosure throughout this specification.

Below, the present disclosure describes a method and apparatus for monitoring a care-receiver using an intelligent robot device. Particularly, in the present disclosure, a device monitoring a care-receiver (hereinafter, referred to as a "monitoring robot device") can move from one place to another place, and can automatically deploy itself in the place. The monitoring robot device can automatically recognize and start monitoring a care-receiver. The monitoring robot device can monitor a baby, an infant or a child who move in the designated area. The monitoring robot device has a map of a home or user area, and a user or guardian can have access to an area map of the monitoring robot device using his/her portable equipment, television, personal computer and the like. The user can designate a virtual boundary on the area map, and instruct the monitoring robot device where and/or how to monitor the care-receiver. The user can rapidly start monitoring the care-receiver using the user device. Also, the user can instruct the monitoring robot device to take care of the care-receiver by helping playing, playing along with the care-receiver, or playing back music/sound corresponding to care-receiver's feelings.

Figure 1:
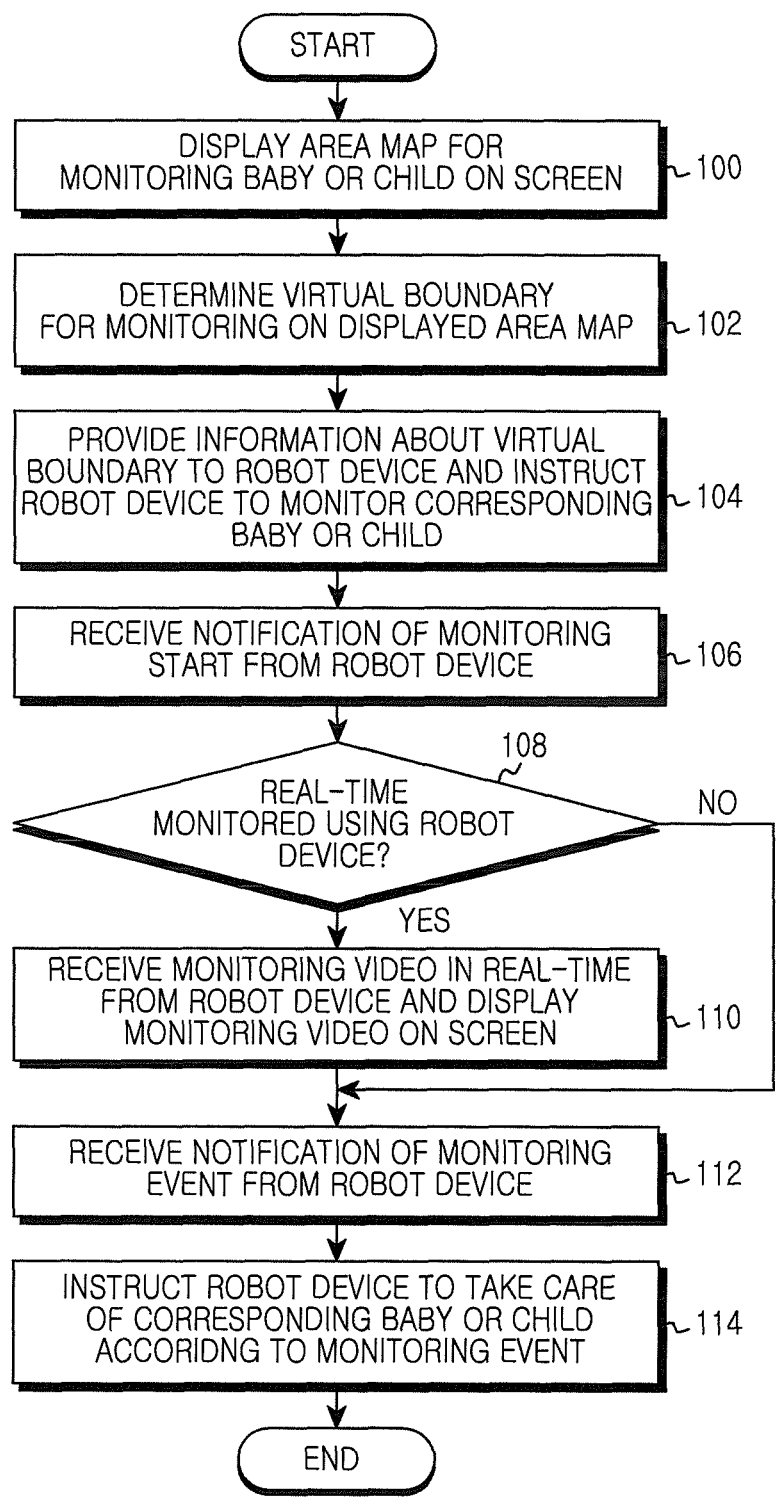
FIG. 1 is a flowchart illustrating an operation of an electronic device of a user or guardian for monitoring according to an exemplary embodiment of the present disclosure.

FIG. 1 illustrates an operation of an electronic device of a user or guardian for monitoring according to an exemplary embodiment of the present disclosure. Referring to FIG. 1, in step 100, an electronic device displays an area map for monitoring a care-receiver on a screen. The area map can be provided by the monitoring robot device, or previously stored in the electronic device of a user through synchronization between the electronic device and the monitoring robot device. Meanwhile, the electronic device, such as a smart phone, a tablet, a smart Television (TV), or a personal computer, can have access to the area map built by the monitoring robot device. The area map can be made from a moving picture or a photograph taken through a camera of the monitoring robot device, and can be zoomed in or out. In one implementation according to the present disclosure, the area map can be made from a moving picture or photograph that the user has transmitted to the monitoring robot device through the electronic device. In another implementation, the area map can be made from a map provided by a server.

After that, in step 102, the electronic device determines a virtual boundary for monitoring a care-receiver, on the displayed area map. In other words, the user or guardian draws the virtual boundary with a hand or electronic pen on the area map displayed on the electronic device (see FIG. 3A and FIG. 4A). The virtual boundary drawn on the area map is to classify districts that the user or guardian determines to be safe although the care-receiver is left alone. An event of notifying the user of alarm when the care-receiver gets out of the virtual boundary on the area map occurs.

After that, in step 104, the electronic device provides information about the virtual boundary drawn by the user, to the monitoring robot device, and instructs the monitoring robot device to monitor the care-receiver. In other words, the user can instruct the monitoring robot device to monitor the care-receiver who is within the range of the area map covered by the monitoring robot device. That is, the user can view the area map of the monitoring robot device using a device such as a smart portable phone, a smart TV or a personal computer, while drawing the virtual boundary on the area map. The user can instruct the monitoring robot device to monitor the care-receiver known within the virtual boundary.

Next, in step 106, the electronic device receives a monitoring start notification from the monitoring robot device. After that, in step 108, the electronic device determines whether to monitor the care-receiver in real-time using the monitoring robot device. When it is determined to monitor the care-receiver in real-time in step 108, the electronic device proceeds to step 110 and receives a real-time monitoring video from the monitoring robot device, displaying the monitoring video on the screen. In contrast, when it is determined not to monitor the care-receiver in real-time in step 108, the electronic device jumps to step 112.

Next, the electronic device proceeds to step 112 and receives a notification of a monitoring event from the monitoring robot device. In an exemplary embodiment, the monitoring event sends a user a notification along with a vibration/alarm sound and the like, for example, through a popup window. Here, the monitoring event occurs when the monitored care-receiver moves out of the virtual boundary, when the monitored care-receiver cries, when a fire or gas leakage occurs around the virtual boundary and the like. Step 110 and step 112 can be carried out independently of each other. That is, step 110 and step 112 can be processed in parallel.

After that, in step 114, the electronic device instructs the monitoring robot device to take care of the care-receiver according, to the notified monitoring event. For example, if the monitoring robot device receives an instruction of monitoring a baby, the monitoring robot device automatically moves to a virtual boundary or near it and discovers a care-receiver known in the virtual boundary. If the monitoring robot device discovers the care-receiver known in the virtual boundary, the monitoring robot device starts monitoring and notifies the user that the monitoring has started. If the monitoring robot device cannot discover the care-receiver known in the virtual boundary, the monitoring robot device notifies the user that the monitoring start has failed. When successfully starting monitoring, the monitoring robot device continuously monitors the care-receiver. The user can instruct the monitoring robot device to notify if the monitored care-receiver moves out of the virtual boundary. The virtual boundary is some area, which is within the area map of the monitoring robot device. While the monitoring robot device monitors, the monitoring robot device automatically changes the directions of a sensor and a camera, which are installed in the monitoring robot device. Also, the user can instruct the monitoring robot device to notify if the care-receiver falls down or cries. At some time point during the monitoring, the user can have access to an audio and a video about the monitored care-receiver using devices such as a smart phone, a smart TV, and a personal computer.

As described above, the monitoring robot device can perform a general monitoring function. The user can instruct the monitoring robot device to monitor a baby who is on a baby cradle or bed. This command is transmitted from a user device such as a smart phone, a TV or a personal computer. The user points out a position of a baby in an area map. If the baby monitoring robot device receives an instruction command, it moves toward an instructed location. The monitoring robot device discovers the baby within the instructed boundary. If discovering the baby within the instructed boundary, the monitoring robot device starts monitoring. Also, the user can instruct the monitoring robot device to notify if the baby cries and wakes up. The monitoring robot device has a capability of being capable of recognizing when the monitored care-receiver wakes up and cries, and a similar action. And, the user can instruct the monitoring robot device to take care of and simultaneously monitor the care-receiver.

Figure 2:
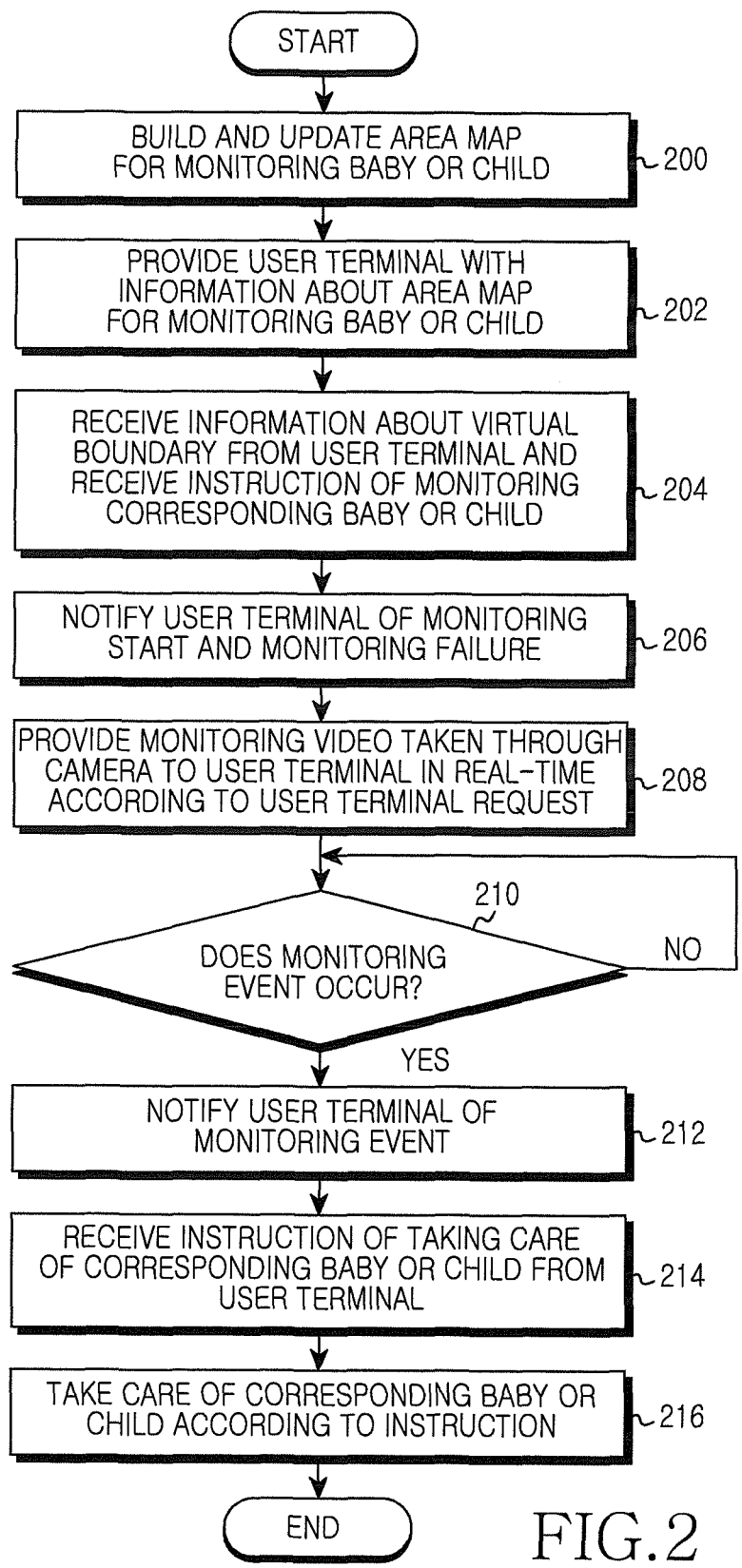
FIG. 2 is a flowchart illustrating an operation of a baby monitoring robot device for baby monitoring according to an exemplary embodiment of the present disclosure.

FIG. 2 illustrates an operation of a monitoring robot device for monitoring a care-receiver according to an exemplary embodiment of the present disclosure. Referring to FIG. 2, in step 200, the monitoring robot device builds and updates an area map for monitoring a care-receiver. Particularly, the monitoring robot device builds and maintains a grid map of area in which a care-receiver is monitored. An area in an area map can be a home of a user, a building, or a specific outdoor space. Also, the area map shows articles and objects in the area. For example, the area map includes a camp bed, a baby cradle, a sofa and the like. It is possible to indicate a specific object in the area map. The monitoring robot device uses a special sensor, a camera, an object sensing technology and the like to accurately build the area map. Also, the monitoring robot device has a function of recognizing a care-receiver and a family. The monitoring robot device can use a technology such as an active vision system and a stereoscopic camera, and other sensor technologies. To obtain effective image information, the active vision system actively controls a position pose of a camera system, or an optic system, and recognizes the outer world through the integration of perception and behavior. The stereoscopic camera is a special camera capable of simultaneously acquiring two sheets of images. If the user views, through a stereo viewer, a photograph acquired using a method of taking a photograph of the same object through two camera lenses spaced at constant intervals, an image can be viewed in three dimensional. And, the monitoring robot device has a night vision function and thus is activated in a dark region. The monitoring robot device can change the direction of the sensor and the camera and easily adjust heights thereof. The monitoring robot device updates the area map by periods and thus, updates some object and article that are in the area on the area map. The precision of the area map is high, so it is possible to show user's objects and articles that are in the area. The monitoring robot device has knowledge of its current location in the map all the time. The monitoring robot device automatically moves to an area of interest and builds an area map. The area map built by the monitoring robot device can be viewed by the user through a device such as a smart phone, a smart TV and a personal computer.

Next, in step 202, the monitoring robot device provides a user terminal with information about the area map for monitoring the care-receiver.

After that, in step 204, the monitoring robot device receives information about a virtual boundary from the user terminal and is instructed to monitor a corresponding care-receiver within the virtual boundary. The monitoring robot device maintains a list of care-receivers to be monitored. The user terminal supports that the monitoring robot device adds or eliminates the care-receiver. It is possible to add a new person to the list of care-receivers by means of a user device such as a smart phone, a smart TV or a personal computer. The monitoring robot device uses or manages a photograph of a care-receiver or a feature thereof, for the sake of recognition. The user can access and view the list of care-receivers of the monitoring robot device, through the user device such as the smart phone, the smart TV or the personal computer.

After that, in step 206, the monitoring robot device searches a care-receiver within the set virtual boundary of the area map, and notifies the user terminal of its search result. For instance, if the care-receiver known within the virtual boundary is searched, the monitoring robot device notifies the user terminal of a monitoring start. If failing to search the care-receiver of the list within the virtual boundary, the monitoring robot device notifies the user terminal of a monitoring failure.

Next, in step 208, the monitoring robot device provides a monitoring image, which is taken by the camera, to the user terminal in real-time according to a user terminal request.

After that, when a monitoring event occurs in step 210, the monitoring robot device proceeds to step 212 and notifies the monitoring event to the user terminal. Here, the monitoring event occurs, for example, when the monitored care-receiver moves out of the virtual boundary, when the monitored care-receiver cries, when a fire or gas leakage occurs around the virtual boundary and the like.

Next, in step 214, the monitoring robot device receives an instruction of taking care of the care-receiver, from the user terminal. After that, in step 216, the monitoring robot device takes care of the care-receiver according to the instruction. In this case, the monitoring robot device can help care-receiver's playing, or play even with the care-receiver. For example, the monitoring robot device can understand care-receiver's feelings using the sensor/camera and the intelligence. Accordingly, the monitoring robot device can play back other music or sound depending on the care-receiver. So, the care-receiver can be continuously stably monitored within the virtual boundary designated by the user. Next, the monitoring robot device terminates the procedure of the present disclosure.

Figure 3A:
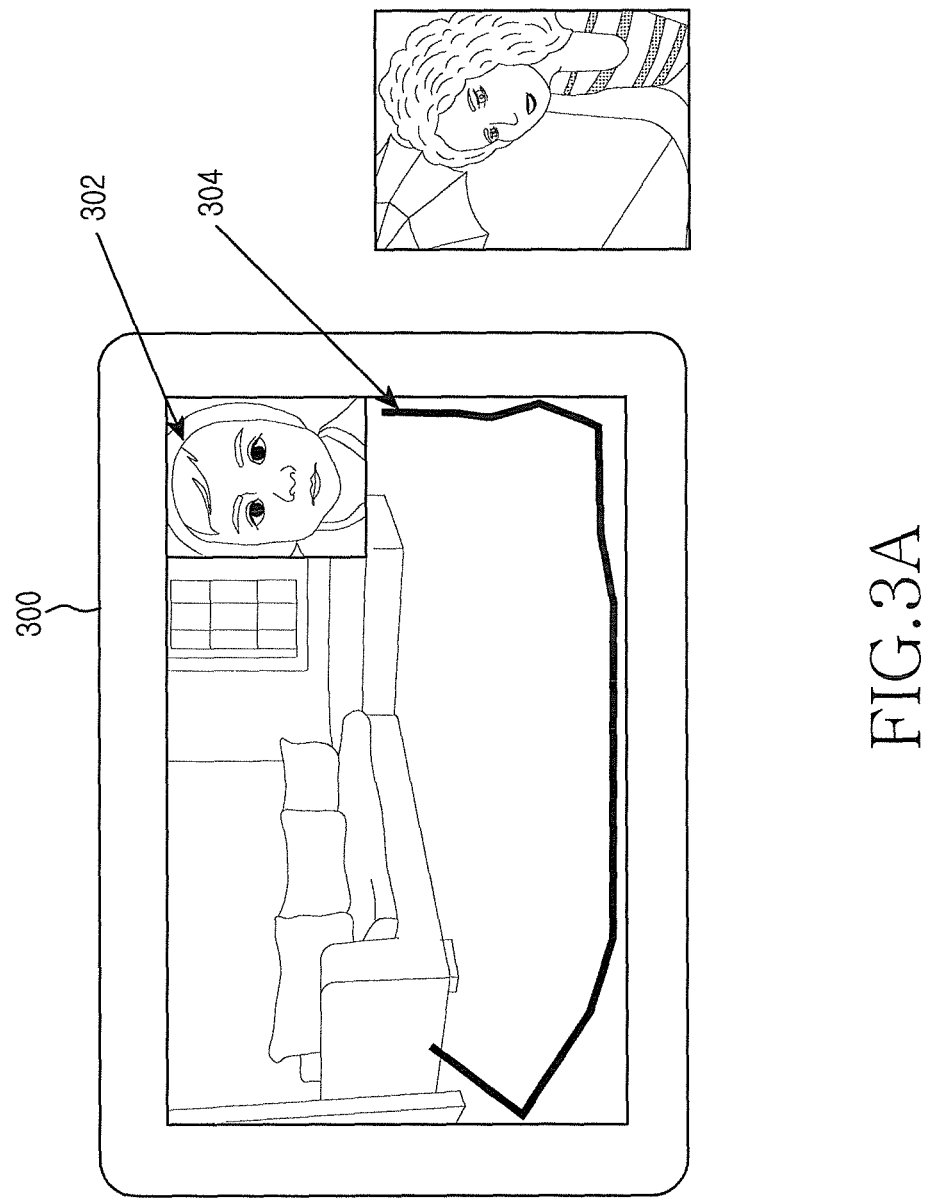
FIGS. 3A to 3C illustrate an example of controlling a baby monitoring robot device using an electronic device of a user according to a first exemplary embodiment of the present disclosure.
Figure 3B:
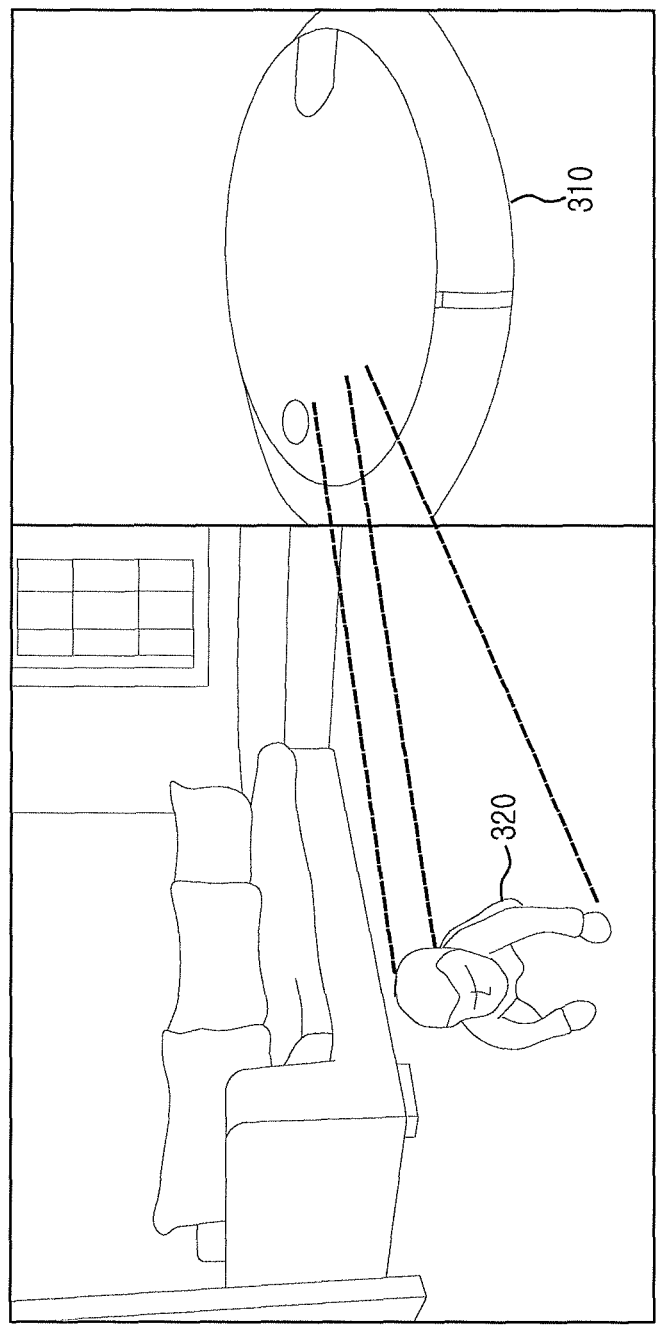
Figure 3C:
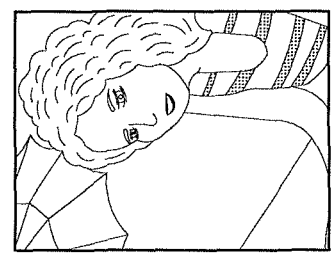
Figure 3C:
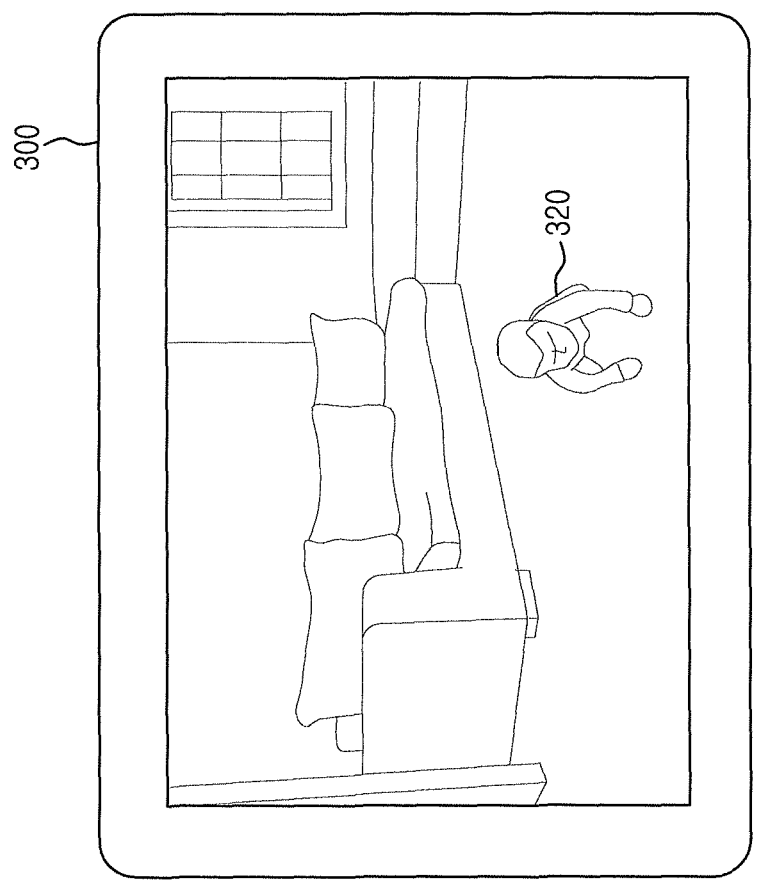

FIGS. 3A to 3C illustrate an example of controlling a monitoring robot device through an electronic device of a user according to a first exemplary embodiment of the present disclosure. FIG. 3A illustrates that an electronic device 300 of a user draws a virtual boundary 304 on the area map of the inside of a house, and instructs a monitoring robot device to monitor a baby 302 of the list of care-receivers. The area map can show a house of the user, a building, or a specific outdoor space as well as articles and objects in the area.

Referring to FIG. 3B, if receiving an instruction, the monitoring robot device 310 automatically moves to a corresponding location of the area map having the virtual boundary. The monitoring robot device 310 automatically discovers a baby 320 who is in an instructed location, and starts monitoring the baby 320. And, the monitoring robot device 310 notifies a guardian who takes care of the baby 320 that the monitoring has started. Whenever the baby 320 moves out of the virtual boundary 304, the guardian who takes care of the baby 320 receives a notification from the monitoring robot device 310. When receiving the notification from the monitoring robot device 310, the guardian who takes care of the baby 320 can go toward the baby 320.

Referring to FIG. 3C, if a user who takes care of a baby 320 wants to watch over the baby 320 in real-time, an electronic device 300 of the user receives a monitoring image from a monitoring robot device 310 in real-time, and displays the monitoring image on a screen.

Figure 4A:
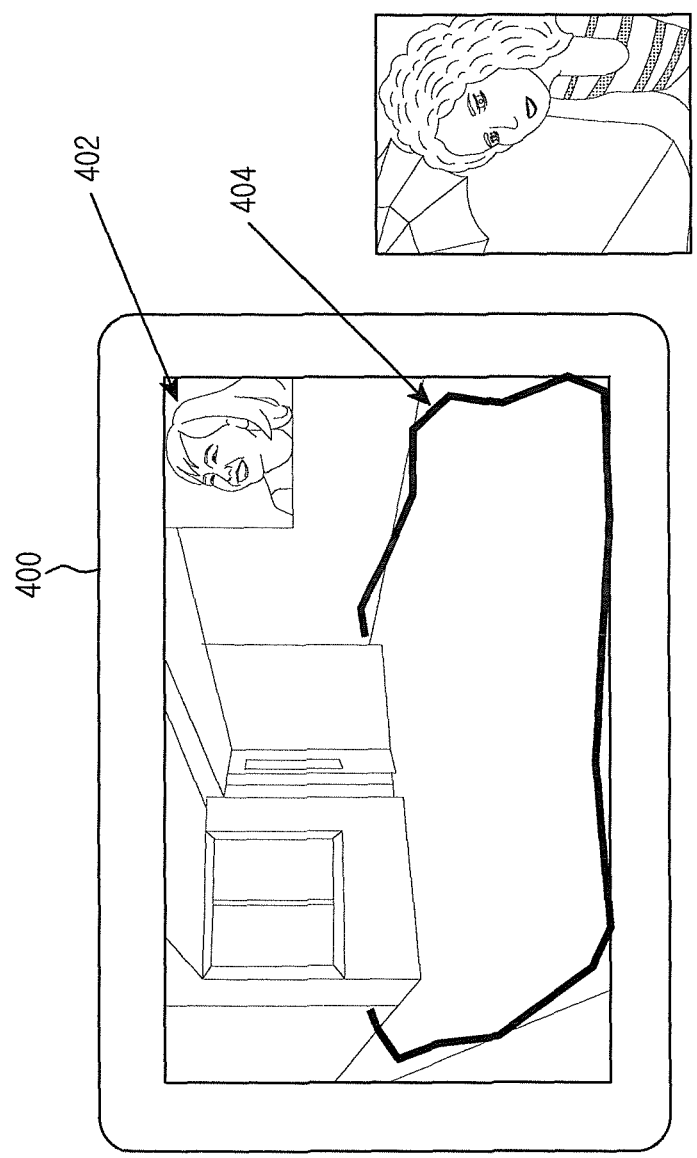
FIGS. 4A to 4C illustrate an example of controlling a monitoring robot device using an electronic device of a user according to a second exemplary embodiment of the present disclosure.
Figure 4B:
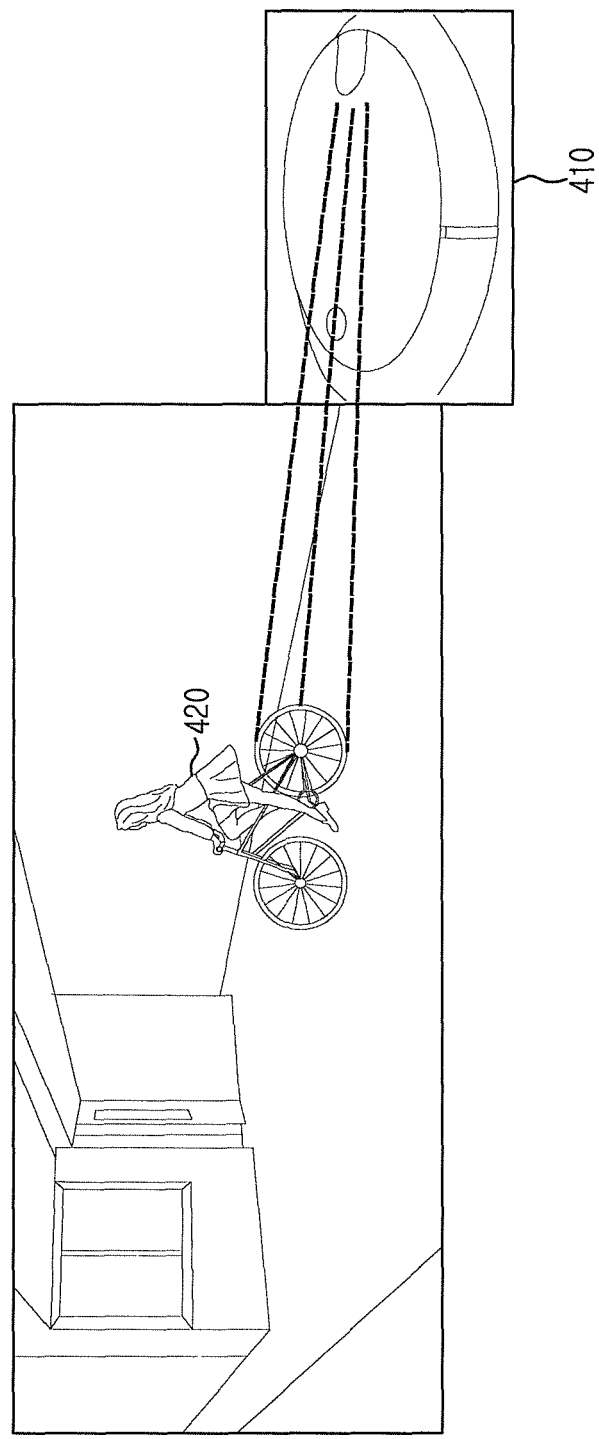
Figure 4C:
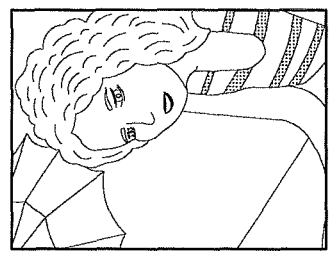
Figure 4C:
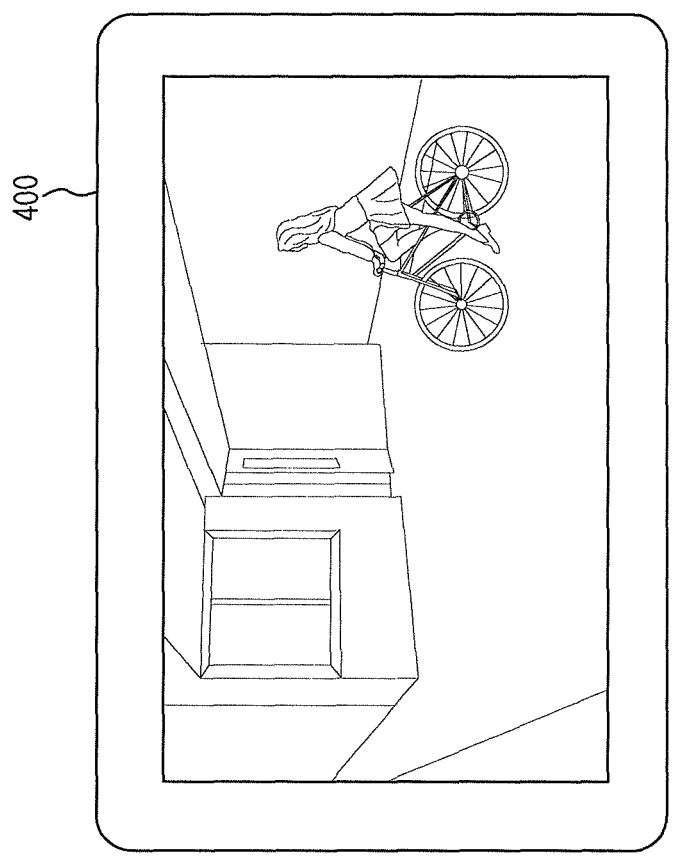

FIGS. 4A to 4C illustrate an example of controlling a monitoring robot device using an electronic device of a user according to a second exemplary embodiment of the present disclosure. FIG. 4A illustrates that an electronic device 400 of a user draws a virtual boundary 404 on an area map of the outside of a house, and instructs a monitoring robot device to monitor a known child 402.

Referring to FIG. 4B, if receiving an instruction, the monitoring robot device 410 automatically moves to the virtual boundary of the area map. The monitoring robot device 410 automatically discovers the child 420 who is in the instructed location, and starts monitoring the child 420. And, the monitoring robot device 410 notifies a guardian who takes care of the child 420 that the monitoring has started. Whenever the child 420 moves out of the virtual boundary 404, the guardian receives a notification from the monitoring robot device 410. When receiving the notification from the monitoring robot device 410, the guardian can go toward the child 420.

Referring to FIG. 4C, if a user who takes care of the child 420 wants to watch over the child 420 in real-time, the electronic device 400 of the user receives a monitoring image from the monitoring robot device 410 in real-time, and displays the monitoring image on a screen.

Figure 5:
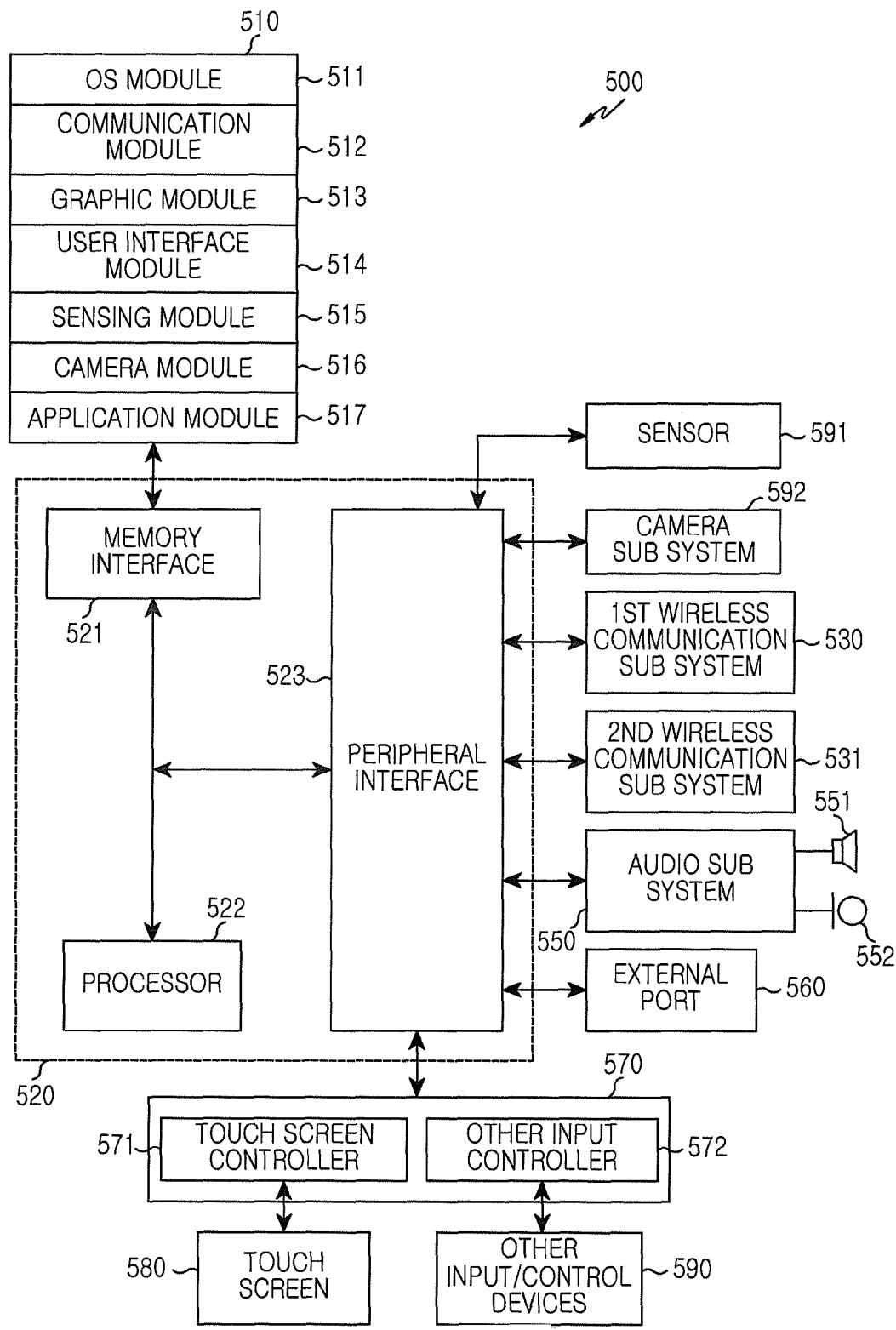
FIG. 5 is a high-level block diagram illustrating a construction of an electronic device for monitoring according to an exemplary embodiment of the present disclosure.

FIG. 5 is a block diagram illustrating a construction of an electronic device 500 according to an exemplary embodiment of the present disclosure. The electronic device 500 can be a portable electronic device, or can be a device such as a portable terminal, a mobile phone, a mobile pad, a media player, a tablet computer, a handheld computer, or a Personal Digital Assistant (PDA). Also, the electronic device 500 can be arbitrary portable electronic device including a device having a combination of two or more functions among these devices.

The electronic device 500 includes a memory 510, a processor unit 520, a 1st wireless communication sub system 530, a 2nd wireless communication sub system 531, an external port 560, an audio sub system 550, a speaker 551, a microphone 552, an Input/Output (I/O) sub system 570, a touch screen 580, and other input or control device 590. The memory 510 and the external port 560 can be used in plural.

The processor unit 520 can include a memory interface 521, one or more processors 522, and a peripheral interface 523. According to cases, the whole processor unit 520 is also called a processor. The memory interface 521, the one or more processors 522, and/or the peripheral interface 523 can be separate constituent elements or can be integrated into one or more integrated circuits.

The processor 522 executes various software programs and performs various functions for the electronic device 500, and also performs processing and control for voice communication and data communication. Also, further to this general function, the processor 522 plays even a role of executing a specific software module (i.e., an instruction set) stored in the memory 510 and performing specific various functions corresponding to the software module. That is, the processor 522 carried out a method of an exemplary embodiment of the present disclosure in inter-operation with the software modules stored in the memory 510.

In an exemplary embodiment of the present disclosure, the processor 522 displays an area map for monitoring a care-receiver, on the touch screen 580, and determines a virtual boundary for monitoring the care-receiver on the displayed area map. The processor 522 provides information about the virtual boundary drawn by a user to a monitoring robot device, and instructs the monitoring robot device to monitor the care-receiver. And, the processor 522 receives a monitoring start notification from the monitoring robot device. Also, the processor 522 determines whether to monitor the care-receiver in real-time using the monitoring robot device. When it is determined to monitor the care-receiver in real-time, the processor 522 real-time receives a monitoring image from the monitoring robot device and displays the monitoring image on the touch screen 580. And if receiving a notification of a monitoring event from the monitoring robot device, the processor 522 instructs the monitoring robot device to take care of the care-receiver according to the notified monitoring event (see FIG. 1).

The processor 522 can include one or more data processors, an image processor, or a COder and DECoder (CODEC). The data processor, the image processor, or the CODEC can be constructed separately. Also, the data processor, the image processor, or the CODEC can include various processors for performing functions different from one another. The peripheral interface 523 connects the input/output sub system 570 of the electronic device 500 and various peripheral devices thereof to the processor 522 and the memory 510 through the memory interface 521.

Various constituent elements of the electronic device 500 can be coupled with one another by one or more communication buses (not denoted by reference numerals) or stream lines (not denoted by reference numerals).

The external port 560 is used for direct connecting the portable electronic device 500 to other electronic devices or indirect connecting the portable electronic device 500 to other electronic devices through a network, for example, the Internet, an intranet, a wireless Local Area Network (LAN) and the like. The external port 560 refers to, for example, a Universal Serial Bus (USB) port or a FIREWIRE port and the like, although not limited to these.

A sensor 591 is coupled to the peripheral interface 523 and enables various functions. For instance, the sensor 591 is coupled to the peripheral interface 523, and can sense a motion of the electronic device 500 and sense a light from the exterior, respectively. Besides this, a positioning system and other sensors such as a temperature sensor, a biological sensor and the like can be connected to the peripheral interface 523 and perform related functions.

A camera sub system 592 can be coupled with the sensor 591 and perform a camera function such as photographing and video clip recording.

A communication function is carried out through one or more wireless communication sub systems 530 and 531. The wireless communication sub systems 530 and 531 can include a radio frequency receiver and transceiver and/or an optical (e.g., infrared) receiver and transceiver. The 1st communication sub system 530 and the 2nd communication sub system 531 can be distinguished according to a communication network in which the electronic device 500 performs communication. For example, the communication network can include a communication sub system designed to operate through a Global System for Mobile Communication (GSM) network, an Enhanced Data GSM Environment (EDGE) network, a Code Division Multiple Access (CDMA) network, a Wireless-Code Division Multiple Access (W-CDMA) network, a Long Term Evolution (LTE) network, an Orthogonal Frequency Division Multiple Access (OFDMA) network, a Wireless Fidelity (Wi-Fi) network, a WiMAX network or/and a Bluetooth network and the like, although not limited to these. The 1st wireless communication sub system 530 and the 2nd wireless communication sub system 531 can be integrated into one wireless communication sub system.

The audio sub system 550 can be coupled to the speaker 551 and the microphone 552 and take charge of input and output of an audio stream such as voice recognition, voice copy, digital recording, and calling function. That is, the audio sub system 550 communicates with a user through the speaker 551 and the microphone 552. The audio sub system 550 receives a data stream through the peripheral interface 523 of the processor unit 520, and converts the received data stream into an electric stream. The converted electric stream is forwarded to the speaker 551. The speaker 551 converts the electric stream into a sound wave audible by a person and outputs the converted sound wave. The microphone 552 converts a sound wave forwarded from the person or other sound sources into an electric stream. The audio sub system 550 receives the converted electric stream from the microphone 552. The audio sub system 550 converts the received electric stream into an audio data stream, and transmits the converted audio data stream to the peripheral interface 523. The audio sub system 550 can include a detachable ear phone, head phone or head set.

The I/O sub system 570 can include a touch screen controller 571 and/or other input controller 572. The touch screen controller 571 can be coupled to the touch screen 580. The touch screen 580 and the touch screen controller 571 can detect a touch and a motion or stopping of them using not only capacitive, resistive, infrared and surface acoustic wave technologies for determining one or more touch points with the touch screen 580 but also an arbitrary multi-touch sensing technology including other proximity sensor arrays or other elements, although not limited to these. The other input controller 572 can be coupled to the other input/control devices 590. One or more buttons (including up/down buttons for adjusting volumes of the speaker 551 and the microphone 552) can be included in the other input/control devices 590. Also, the button can be a push button, a rocker button and the like. The button can be a rocker switch, a thumb-wheel, a dial, a stick, and/or a pointer device such as a stylus and the like.

The touch screen 580 provides input/output interface between the electronic device 500 and the user. That is, the touch screen 580 forwards a user's touch input to the electronic device 500. Also, the touch screen 580 is a medium for displaying an output of the electronic device 500 for the user. That is, the touch screen 500 displays a visual output for the user. This visual output is displayed in a form of a text, a graphic, a video and a combination of them.

In the present disclosure, when the electronic device 500 outputs an area map, the area map can be output through a screen. This screen can be also a touch screen processing a touch input.

The touch screen 580 can be various displays. For instance, the touch screen 580 can be a Liquid Crystal Display (LCD), a Light Emitting Diode (LED), a Light emitting Polymer Display (LPD), an Organic Light Emitting Diode (OLED), an Active Matrix Organic Light Emitting Diode (AMOLED) or a Flexible LED (FLED), although not limited to these.

The memory 510 can be coupled to the memory interface 521. The memory 510 can include one or more high-speed random access memories and/or non-volatile memories such as magnetic disk storage devices, and one or more optical storage devices and/or flash memories (for example, NAND or NOR).

The memory 510 stores software. A software constituent element includes an Operating System (OS) module 511, a communication module 512, a graphic module 513, a user interface module 514, a sensing module 515, a camera module 516, one or more application modules 517 and the like. Also, because the module, the software constituent element, can be expressed as a set of instructions, the module is also called an instruction set. The module is also expressed as program.

The OS software 151 (e.g., a built-in operating system such as WINDOWS, LINUX, Darwin, RTXC, UNIX, OS X, or VxWorks) includes various software constituent elements controlling general system operation. Control of the general system operation means, for example, memory management and control, storage hardware (device) control and management, power control and management and the like. The OS software 151 performs even a function of making smooth communication between various hardware and software constituent elements.

The communication module 512 can enable communication with other electronic devices such as a personal computer, a server and/or a portable terminal, through the 1st and 2nd wireless communication sub systems 530 and 531 or the external port 560.

The graphic module 513 includes various software constituent elements for providing and displaying a graphic on the touch screen 580. The term 'graphic' includes a text, a web page, an icon, a digital image, a video, an animation and the like.

The user interface module 514 includes various software constituent elements associated with a user interface. The user interface module 514 includes information about how a state of the user interface is changed or in which conditions the change of the state of the user interface is carried out, and the like.

The sensing module 515 can sense an area map of the monitoring robot device and can help the monitoring robot device to add a new monitoring target such as baby/infant/child into a monitoring target list, and includes information about instructing where, how the baby/infant/child of the list is to be monitored.

The camera module 216 includes a camera related software constituent element enabling a camera-related process and function. The application module 517 includes a browser, an electronic mail (e-mail), an instant message, word processing, keyboard emulation, an address book, a touch list, a widget, Digital Right Management (DRM), voice recognition, voice copy, a location determining function, a location-based service and the like. The memory 510 can include additional modules (i.e., instructions) besides the above-mentioned modules. Or, the memory 510 cannot use some modules (i.e., instructions) according to need.

Also, various functions of the electronic device 500 according to the present disclosure mentioned above or to be mentioned below can be executed by hardware including one or more stream processing and/or Application Specific Integrated Circuit (ASIC), software and/or a combination of them.

Figure 6:
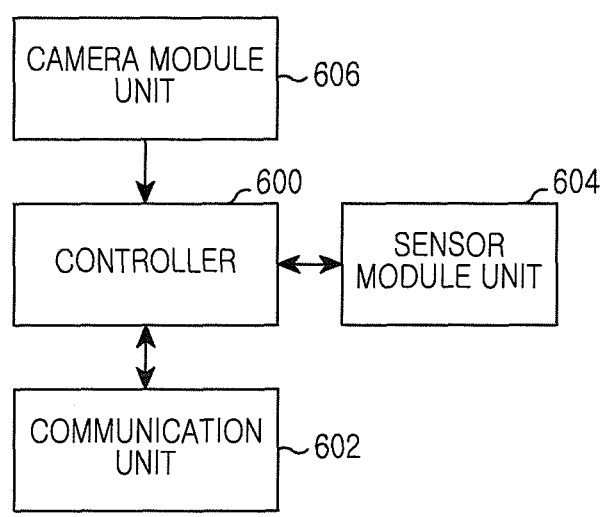
FIG. 6 is a block diagram illustrating a construction of a monitoring robot device for monitoring according to an exemplary embodiment of the present disclosure.

FIG. 6 illustrates a monitoring robot device for monitoring according to an exemplary embodiment of the present disclosure. Referring to FIG. 6, the monitoring robot device includes a controller 600, a communication unit 602, a sensor module unit 604, and a camera module unit 606. The controller 600 performs general control of the monitoring robot device, and performs an operation for monitoring a baby or child according to the present disclosure. For example, the controller 600 builds and updates an area map for monitoring the baby or child. And, the controller 600 maintains a list of known persons to be monitored.

The area map is commonly a house of a user, a building, or a specific outdoor space. The area map shows articles and objects in the area. For example, the area map shows a camp bed, a baby cradle, a sofa and the like. The controller 600 uses a special sensor, a camera, an object sensing technology and the like to accurately build the area map. Also, based on the special sensor, the camera, and the object sensing technology, the controller 600 recognizes a baby/infant/child of the list to be monitored. In addition, the controller 600 can use a technology such as an active vision system and a stereoscopic camera, and other sensor technologies. And, the controller 600 controls a night vision function and thus, supports an operation of the monitoring robot device in a dark region. The controller 600 can move the direction of the sensor and the camera and easily adjust heights thereof.

The controller 600 provides information about the area map for monitoring the baby or child to a user terminal through the communication unit 602, and receives information about a virtual boundary and an instruction of instructing to monitor a corresponding baby or child, from the user terminal. Also, the controller 600 discovers the baby or child known within the set virtual boundary of the area map, and notifies its discovery result to the user terminal. For example, if the baby or child of the list within the virtual boundary is searched, the controller 600 notifies the user terminal of monitoring start. If it fails to search the baby or child of the list within the virtual boundary, the controller 600 notifies the user terminal of monitoring failure.

The controller 600 provides a monitoring video, which is taken through the camera module unit 606, to the user terminal through the communication unit 602 in real-time according to a user terminal request. And, when a monitoring event occurs, the controller 600 notifies the user terminal of the monitoring event. Here, the monitoring event occurs, for example, when a monitored baby/infant/child moves out of the virtual boundary, when the monitored baby/infant/child cries, or when a fire or gas leakage occurs around the virtual boundary or the like.

Also, when the controller 600 receives an instruction of taking care of a baby or child from the user terminal, the monitoring robot device can help a baby/infant/child play, or play even with a baby/infant/child. For instance, the monitoring robot device can understand baby/infant/child's feeling using the sensor/camera and the intelligence. Accordingly, the monitoring robot device can play back other music or sound according to feeling of the baby/infant/child.

The communication unit 602 can include a radio frequency receiver and transceiver and/or optical (e.g., infrared) receiver and transceiver. The communication unit 602 can be distinguished according to a communication network in which the monitoring robot device performs communication. For instance, the communication network can include a communication sub system designed to operate through a GSM network, an EDGE network, a CDMA network, a W-CDMA network, an LTE network, an OFDMA network, a Wi-Fi network, a WiMAX network or/and a Bluetooth network and the like.

The sensor module unit 604 provides a sensed signal to the controller 600 using a plurality of sensors. The sensed signal is used for accurately building an area map or recognizing a baby/infant/child. For one instance, the sensor module unit 604 provides the result to the controller 600 using an object sensing sensor.

The camera module unit 606 changes a camera direction according to a motion of an object monitored by the sensor module unit 604, takes a video, and provides the video to the controller 600. The controller 600 analyzes a signal provided from the sensor module unit 604 and the camera module unit 606, and recognizes articles and objects within the area map. Also, the controller 600 can use a technology such as an active vision system and a stereoscopic camera, and other sensor technologies. And, the controller 600 has a night vision function and thus, controls the monitoring robot device to operate in a dark region.

As described above, exemplary embodiments of the present disclosure have an advantage that a guardian can intelligently and efficiently monitor a care-receiver, by automatically monitoring the baby or child in a location designated by the guardian, transmitting a monitoring event to the guardian, and taking a corresponding action for the baby or child according to a guardian's instruction.

Embodiments of the present invention according to the claims and description in the specification can be realized in the form of hardware, software or a combination of hardware and software.

Such software may be stored in a computer readable storage medium. The computer readable storage medium stores one or more programs (software modules), the one or more programs comprising instructions, which when executed by one or more processors in an electronic device, cause the electronic device to perform methods of the present invention.

Such software may be stored in the form of volatile or non-volatile storage such as, for example, a storage device like a ROM, whether erasable or rewritable or not, or in the form of memory such as, for example, RAM, memory chips, device or integrated circuits or on an optically or magnetically readable medium such as, for example, a CD, DVD, magnetic disk or magnetic tape or the like. It will be appreciated that the storage devices and storage media are embodiments of machine-readable storage that are suitable for storing a program or programs comprising instructions that, when executed, implement embodiments of the present invention. Embodiments provide a program comprising code for implementing apparatus or a method as claimed in any one of the claims of this specification and a machine-readable storage storing such a program. Still further, such programs may be conveyed electronically via any medium such as a communication signal carried over a wired or wireless connection and embodiments suitably encompass the same. While the disclosure has been shown and described with reference to certain preferred embodiments thereof, it will be understood by those skilled in the art that various changes in form and details can be made therein without departing from the spirit and scope of the invention as defined by the appended claims.

What is claimed is:

1. A method for monitoring in a monitoring robot device, the method comprising:
   obtaining and transmitting, by the monitoring robot device, an area map to an electronic device communicating with the monitoring robot device;
   receiving, from the electronic device, a boundary on the area map for monitoring whether a monitored target is located within the boundary, wherein the boundary is drawn on the transmitted area map by a user's touch input via a screen of the electronic device;
   in response to receiving the boundary on the area map, automatically moving the monitoring robotic device, by the monitoring robotic device, to a corresponding location of the area map having the boundary and determining whether the monitored target is inside the boundary on the area map, wherein the monitored target comprises at least one target identified based on a list including one or more predetermined monitored targets;
   when the monitored target is not located within the boundary on the area map, transmitting an alarm event to the electronic device; and
   in response to receiving an instruction from the electronic device, tracking the monitored target and providing a caring service to the monitored target within the boundary on the area map.

2. The method of claim 1, further comprising obtaining a monitoring video via a camera, wherein the area map is obtained from the monitoring video.

3. The method of claim 1, wherein the area map is generated using at least one sensor of the monitoring robot device.

4. The method of claim 1, further comprising transmitting a monitoring video associated with the area map to the electronic device.

5. The method of claim 1, further comprising providing an access to a monitoring video associated with the monitored target to a user.

6. The method of claim 1, wherein the boundary is drawn on the area map by the user's touch input using a finger or an electronic pen.

7. The method of claim 1, wherein the alarm event comprises at least one of vibration, a pop up message, or an alarm sound.

8. The method of claim 1, wherein the alarm event comprises an instruction of giving an appropriate service to the monitored target.

9. The method of claim 1, wherein the monitored target comprises a human.

10. A monitoring robot device comprising:
    a camera;
    a sensor module unit;
    a communication module configured to communicate with an electronic device; and
    a controller configured to:
      obtain and transmit, by the monitoring robot device, an area map to the electronic device communicating with the monitoring robot device;
      receive, from the electronic device, a boundary on the area map for monitoring whether a monitored target is located within the boundary, wherein the boundary is drawn on the transmitted area map by a user's touch input via a screen of the electronic device;
      in response to receiving the boundary on the area map, automatically move the monitoring robot device to a corresponding location of the area map having the boundary and determine whether the monitored target is inside the boundary on the area map, wherein the monitored target comprises at least one target identified based on a list including one or more predetermined monitored targets;
      when the monitored target is not located within the boundary on the area map, transmit an alarm event to the electronic device; and
      in response to receiving an instruction from the electronic device, track, with the monitoring robot device, the monitored target and provide a caring service to the monitored target within the boundary on the area map.

11. The monitoring robot device of claim 10, wherein the controller is further configured to transmit the area map to the electronic device.

12. The monitoring robot device of claim 10, wherein the controller is further configured to obtain a monitoring video via the camera, wherein the area map is obtained from the monitoring video.

13. The monitoring robot device of claim 10, wherein the area map is generated using at least one sensor of the monitoring robot device.

14. The monitoring robot device of claim 10, wherein the controller is further configured to transmit a monitoring video, associated with the area map, to the electronic device.

15. The monitoring robot device of claim 10, wherein the controller is further configured to provide an access to a monitoring video associated with the monitored target to a user.

16. The monitoring robot device of claim 10, wherein the boundary is drawn on the area map by the user's touch input using a finger or an electronic pen.

17. The monitoring robot device of claim 10, wherein the alarm event comprises at least one of vibration, a pop up message, or an alarm sound.

18. The monitoring robot device of claim 10, wherein the alarm event comprises an instruction of giving an appropriate service to the monitored target.

19. The monitoring robot device of claim 10, wherein the monitored target comprises a human.

* * * * *